United States Patent [19]
Carty et al.

[11] Patent Number: 4,917,889
[45] Date of Patent: Apr. 17, 1990

[54] TOPICAL COMPOSITION AND TREATMENT

[75] Inventors: Barbara A. Carty, Bronx; Anna Grealish, Yonkers, both of N.Y.; Mary Murtagh, Saddle Brook, N.J.

[73] Assignee: Thomas W. Clarke, Midland, N.J.; a part interest

[21] Appl. No.: 218,897

[22] Filed: Jul. 14, 1988

[51] Int. Cl.⁴ .............................................. A61K 33/08
[52] U.S. Cl. .................................................. 424/693.1
[58] Field of Search ......................................... 424/157

[56] References Cited
PUBLICATIONS

Chem. Abst., 87-116663u, (1977).

*Primary Examiner*—Stanley J. Friedman

[57] ABSTRACT

Methods and compositions for the topical treatment of burns, bedsores and other skin afflications are disclosed which comprise the topical application to affected areas of the skin of a composition comprising an aqueous mixture of calcium hydroxide and a fixed drying oil.

4 Claims, No Drawings

TOPICAL COMPOSITION AND TREATMENT

This invention relates to novel compositions for the treatment of burns, bedsores and other skin afflictions. More particularly, this invention relates to novel compositions for the topical treatment of skin lesions caused by the application of pressure, heat or fire to the skin and to a reduction in scarring of the skin as a result of such lesions.

Decubitus ulcer, more commonly known as bedsore; pressure sore or trophic ulcer, is the ischemic necrosis and ulceration of skin tissue overlying a bony prominence of the body that has been subjected to prolonged pressure against an object such as a cushion, mattress, cast, splint, etc.

The condition is most frequently found in patients who have been bedridden for long periods of time such as the aged or infirmed and particularly among those with severely diminished or totally absent sensation, such as those suffering from debilitation, emaciation or paralysis induced by physical injury or neurologic disorder.

Tissues over the sacrovertebral area, the pelvic area, the lower pelvic and thigh area, as well as the ankles, heels and elbows are especially susceptible to development of decubitus ulcers but other sites may also be involved depending upon the positions of the particular patient.

In its most serious presentations, decubitus ulcer may also effect muscle and bone as well as the epidermis and dermis. These more serious decubitus ulcers require surgical removal and skin grafting for closure.

The best treatment for bedsores is prevention, i.e., frequent changing of the bedridden patients position and providing even distribution of the patient's weight. The latter may be accomplished through the use of an anti-bed-sore mattress or cushion such as disclosed in French Patent No. 2,598,910; U.S. Pat. Nos. 4,653,130; 4,517,693; 4,610,253 and French Patent No. 2,471,185.

Burns to which the topical formulations of the present invention may be applied are burns of the first degree, those which show redness of the skin; second degree, those which show vesication of the skin; and third degree, those which produce necrosis through the entire skin.

Wound dressings suitable for use in treating burns, bedsores, etc. are disclosed in U.S. Pat. Nos. 4,300,575; 3,903,882; 3,949,071 and Canadian Patent No. 1,212,879. Moreover, it has been found that the timely application of the compositions of the present invention substantially reduces or eliminates the occurrence of scarring as a result of such burns, bedsores, etc.

Prior to the present invention, while many dressings and topical agents have been available for use in the treatment of burns, bedsores, etc., they are as a rule all expensive and in many cases totally useless.

The present invention is concerned with inexpensive, highly effective compositions for the treatment of burns, bedsores and other skin afflictions which comprises a mixture of an aqueous solution of calcium hydroxide and a fixed drying oil, such as linseed oil.

Calcium hydroxide topical solutions commonly referred to as lime water are described in The Official Monographs at page 109 of the 1980 Edition of the U.S. Pharmacopia National Formulary.

The solutions generally contain not less than 0.14 gm. of $Ca(OH)_2$ per 100 cc. of water at 25° C. and are prepared by adding 3 grams of calcium hydroxide to purified water with vigorous mixing for at least one hour. The excess calcium hydroxide is allowed to settle. The film of calcium carbonate forming on the surface is skimmed and only the clear supernatant liquid is decanted and utilized in the formulations of the present invention. Moreover, the undissolved portion or slaked lime is not suitable for preparing additional quantities of calcium hydroxide solution.

The calcium hydroxide content of the solutions is directly related to the temperature of the water during processing as well as the temperature at which the finished solution is stored. The calcium hydroxide content at 15° C. is about 0.17 gm. per 100 cc. and less at higher temperatures. The official concentration is determined at 25° C.

The fixed drying oils useful in the preparation of the compositions of the present invention are the oils obtained from seeds such as flax seed oil, commonly known as linseed oil, walnut seed oil, poppy seed oil, hemp seed oil and sunflower seed oil. The pharmaceutical grade of raw linseed oil, the preferred fixed drying oil employed in the present invention is readily available on a commercial basis.

The ratio of aqueous calcium hydroxide solution to fixed drying oil employed in the present invention can be varied over wide limits, however, a mixture of equal parts aqueous calcium hydroxide and fixed drying oil is preferred.

A preferred composition and method for carrying out the present invention is illustrated by the following example:

EXAMPLE

Sixteen ounces of water are combined with six ounces of lime, which when freshly ignited to constant weight, contains not less 95.0 percent of CaO, and the mixture allowed to stand for twelve hours after which a film composed primarily of calcium carbonate is skimmed from the surface of the mixture and the upper aqueous phase of the mixture is decanted and filtered. Four ounces of raw linseed oil is slowly added to four ounces of the filtrate and the mixture vigorously stirred until the mixture thickens which is on the order of about three minutes.

The thickened mixture is applied directly to the burn, bedsore or otherwise affected skin area and the area maintained in a moistened condition.

While the preferred mode of application is to daube the mixture directly onto the affected skin area, the compositions of the present invention may also be sprayed or combined with suitable pharmaceutical carriers or bases for application.

Moreover, while best results are achieved using freshly made up compositions, the compositions may be stored in well filled, tight containers at temperatures not exceeding 25° C.

Numerous modifications and variations of the present invention are possible in light of the above teachings and therefore within the scope of the appended claims, and the invention may be practiced otherwise than as particularly described.

We claim:

1. A composition suitable for the topical treatment of burns and sores consisting essentially of about equal parts of an aqueous solution of calcium hydroxide containing not less than about 0.14 grams of $Ca(OH)_2$ per 100 cc. of water at 25° C. and raw linseed oil.

2. A method of treating burns and sores on the skin of warm-blooded animals in need of such treatment which comprises applying to said burns and sores a mixture consisting essentially of from about equal parts of an aqueous solution of calcium hydroxide containing not less than about 0.14 grams of $Ca(OH)_2$ per 100 cc. of water at 25° C. and a fixed drying oil.

3. A method as claimed in claim 2 wherein said fixed drying oil is selected from the group consisting of walnut oil, poppy oil, hemp oil, sunflower oil and linseed oil.

4. A method as claimed in claim 2 wherein said fixed drying oil is raw linseed oil.

* * * * *